(12) United States Patent
Hattori

(10) Patent No.: US 6,306,344 B1
(45) Date of Patent: Oct. 23, 2001

(54) METHOD FOR RETAINING OR ENRICHING γ-AMINOBUTYRIC ACID IN GREEN GRASS LEAVES

(75) Inventor: Toshimitsu Hattori, Fukuoka (JP)

(73) Assignee: Toyo Shinyaku Co., Ltd. (JP)

(*) Notice: Subject to any disclaimer, the term of this patent is extended or adjusted under 35 U.S.C. 154(b) by 0 days.

(21) Appl. No.: 09/557,128

(22) Filed: Apr. 25, 2000

(30) Foreign Application Priority Data

Apr. 26, 1999 (JP) .................................................. 11-117734
Jul. 19, 1999 (JP) .................................................. 11-204060

(51) Int. Cl.[7] ........................ A61K 41/00; A61K 35/78; A61K 31/197
(52) U.S. Cl. ................................ 422/21; 422/1; 424/750; 424/774; 562/554; 562/574
(58) Field of Search ................................ 424/195.1, 774, 424/750; 422/21, 40, 1; 562/553, 554, 574

(56) References Cited

FOREIGN PATENT DOCUMENTS

| | | |
|---|---|---|
| 63-269948 | * 11/1988 | (JP) . |
| 2544302 | 10/1996 | (JP) . |
| 11-75791 | 3/1999 | (JP) . |

OTHER PUBLICATIONS

Dabrowska et al. "Free amino acids in leaves and inforescences of grass species," Acta Soc. Bot. Pol. 39(3), pp. 445–452, 1970.*

Rymowicz–Dabroska et al. "Free amino acids in fodder plants. III. Free amino acids in various organs of some grass species," Rocz. Nauk Roln., Ser. A, 97(1), pp. 15–19, 1970.*

Tomlinson et al. Abstract of "Metabolic changes in free amino acids of bean leaves exposed to ozone," Phytopathology (1967), 57(9), pp. 972–974.*

* cited by examiner

Primary Examiner—Elizabeth McKane
(74) Attorney, Agent, or Firm—Webb Ziesenheim Logsdon Orkin & Hanson, P.C.

(57) ABSTRACT

The present invention provides a method for retaining or enriching γ-aminobutyric acid in green grass leaves, which comprises the step of subjecting green grass leaves or processed products thereof to at least one treatment selected from the group consisting of incubation treatment, anaerobic treatment, and microwave treatment.

10 Claims, No Drawings

METHOD FOR RETAINING OR ENRICHING γ-AMINOBUTYRIC ACID IN GREEN GRASS LEAVES

BACKGROUND OF THE INVENTION

1. Field of the Invention

The present invention relates to a method for retaining or increasing the content of γ-aminobutyric acid having an antihypertensive function in the green leaves of grass plants.

2. Description of the Related Art

Green leaves of grass plants, such as the young leaves of barley, wheat, rye, oats, adlay, Italian ryegrass, rice, and the like, are rich in vitamins, minerals, dietary fiber, and so on. They have therefore received attention for their usability as materials for health food products that provide the effects of adsorbing harmful substances, improving the intestinal environment, suppressing absorption of cholesterol, preventing the postprandial sudden rise in blood sugar, activating superoxide dismutase (SOD), and the like. When such young leaves, for example, are used as a material for health foods, they are presented in various forms. For instance, the young leaves of barley are directly dried and powdered to obtain leaf powder (Japanese Patent No. 2544302), or processed into the forms of juice, extract, and powder of such juice and extract (Japanese Laid-Open Patent Publication No. 11-75791). In either case, products having useful ingredients such as dietary fiber and vitamins retained therein in a larger amount are more preferable.

Green grass leaves contain enzymes such as chlorophyllase, peroxidase, and polyphenol oxidase that cause degeneration such as the fading of the vivid green color of green leaves. In order to prevent such degeneration, green leaves are generally subjected to hydrothermal treatment (i.e., blanching). During this treatment, ingredients naturally contained in green leaves, such as vitamins, minerals, and chlorophyll, tend to be lost.

SUMMARY OF THE INVENTION

The present inventors have investigated unknown active ingredients contained in green grass leaves and found that green grass leaves contain γ-aminobutyric acid (hereinafter, may be abbreviated as GABA) that is known as an antihypertensive substance. It has also been found that GABA is conventionally lost during the steps of processing green grass leaves, for example, at various stages for producing food materials using green grass leaves.

The method for retaining or enriching γ-aminobutyric acid in green grass leaves of the present invention comprises the step of subjecting green grass leaves or processed products thereof to at least one treatment selected from the group consisting of incubation treatment, anaerobic treatment, and microwave treatment.

In a preferred embodiment, the green grass leaves or processed products thereof are subjected to at least one treatment selected from the group of incubation treatment and anaerobic treatment.

In a preferred embodiment, the grass is at least one selected from the group consisting of barley, wheat, rye, oats, adlay, Italian ryegrass, and rice.

In a preferred embodiment, the green grass leaves containing retained or enriched γ-aminobutyric acid is in a form of green leaves, green leaf dried products, powder of green leaf dried products, green leaf fragments, dried green leaf fragments, green leaf juice, powder obtained from green leaf juice, green leaf extract, or powder obtained from green leaf extract.

In a preferred embodiment, the above-mentioned method further comprises the step of treating the green grass leaves containing retained or enriched γ-aminobutyric acid by the microwave treatment.

Thus, the present invention makes possible the objects of: providing a method for retaining the content of γ-aminobutyric acid, known as an antihypertensive substance, in green grass leaves for a prolonged period of time or enriching the γ-aminobutyric acid; providing a method for retaining the content of γ-aminobutyric acid in green grass leaves for a prolonged period of time or enriching the γ-aminobutyric acid, wherein not only the γ-aminobutyric acid but also other ingredients naturally contained in the green grass leaves remain in large amounts; and a method as described above wherein the treated green grass leaves have a vivid green color and are excellent in preservation stability and palatability.

DESCRIPTION OF THE PREFERRED EMBODIMENTS

The present inventors have intensively examined ingredients naturally contained in green grass leaves and found that the green leaves contain γ-aminobutyric acid (GABA), known as an antihypertensive substance. It has also been found that GABA is conventionally lost during the steps of processing green grass leaves, for example, at various stages for producing food materials using green grass leaves. Further examination by the present inventors has revealed that if green grass leaves or processed products thereof are subjected to at least one of incubation treatment, anaerobic treatment, and microwave treatment, the γ-aminobutyric acid content in the resultant green grass leaves or processed products thereof can be retained or increased. Furthermore, the resultant green grass leaves or processed products thereof contain active ingredients such as vitamins (in particular, water-soluble vitamins), minerals, and chlorophyll in larger amounts and are free from fading of the vivid green color of the green leaves and from changing in flavor. The present invention is based on these results of this examination.

As used herein, the term "grass" refers to all the plants belonging to the Gramineae family in the botanical classification. Concrete examples of grass plants include, but are not limited to, barley, wheat, rye, oats, adlay, Italian ryegrass, Italian ace, rice, foxtail millet, bamboo grass, Japanese millet, millet, corn, sorghum, and sugar cane. Among these, barley, wheat, rye, oats, adlay, Italian ryegrass, rice, and the like are especially preferable.

As used herein, the term "green grass leaves" refers to the leaves and/or stems of a harvested grass plant. The green leaves are preferably young leaves prematurely harvested. The term "processed products" of green leaves refers to processed products of the above-defined leaves and/or stems of a harvested grass plant in various forms.

Young leaves of at least one of barley, wheat, rye, oats, adlay, Italian ryegrass, and rice are preferably used. Such young leaves are preferably harvested during the period from the start of branching until the early days of earring (when the stem length is about 20 to 40 cm). Young barley leaves are more preferable.

According to the present invention, green grass leaves or processed products thereof are subjected to at least one treatment selected from the group consisting of incubation treatment, anaerobic treatment, and microwave treatment.

Green grass leaves are preferably subjected to the treatment immediately after harvest. If time is required before treatment, the leaves may be stored by a storage means known to those skilled in the art, such as cold storage, for preventing degeneration.

Harvested green leaves may be directly subjected to any of the treatments described above (details to follow). As required, green leaves are washed with water, preferably 25° C. or lower cold water, to remove dirt attached thereto. After being drained, the green leaves are cut into an appropriate length (e.g., 10 cm for young leaves of grass plants such as wheat, rye, oats, adlay, Italian ryegrass, and rice) as required.

Examples of processed products of green leaves include green leaf fragments and green leaf juice. The green leaf fragments include cut products having a size easy to treat and green leaf slurry.

The cut products are obtained by a method for cutting a plant into pieces generally used by those skilled in the art, such as slicing and shredding. The slurry is obtained by crushing green leaves with a crusher such as a juicer, a mixer, or a blender. By this processing, the green leaves are changed to a thick suspension including liquid and solids having certain fluidity. The green leaf juice is obtained by squeezing green leaves directly or after they have been fragmented. Alternatively, the green leaf juice is obtained by centrifuging or filtering green leaf slurry.

By subjecting green grass leaves or processed products thereof to at least one of incubation treatment and anaerobic treatment, the GABA originally contained in the green leaves is enriched.

Incubation treatment may be effected by any appropriate means including heat retaining treatment with the use of hot water, infrared irradiation, and heat retaining treatment with the use of an incubator. The temperature for the incubation treatment is preferably about 20 to 50° C., more preferably about 30 to 45° C., and most preferably 40° C. or around 40° C. If the temperature is lower than 20° C. or higher than 50° C., the increase in GABA content is reduced.

Anaerobic treatment refers to a treatment with (i.e., contact with) a gas containing little oxygen or no oxygen at all, including treatment in the vacuum state. As such a gas, carbon dioxide gas and nitrogen gas are preferably used.

GABA can be sufficiently enriched by being subjected to incubation treatment or anaerobic treatment for ten minutes or longer. Such a treatment is generally continued for 10 minutes to 24 hours, preferably for 1 to 12 hours. With treatment for 30 minutes or longer, the GABA content increases twofold or more. A combination of the incubation treatment and the anaerobic treatment is recommended.

The GABA content of the thus-obtained green leaves is usually higher than that of those subjected to no GABA enriching treatment by twofold or more, preferably threefold or more, more preferably fivefold or more.

By subjecting green grass leaves or processed products thereof to microwave treatment, the reduction in GABA content during the processing of the green grass leaves or the reduction in GABA content with time is minimized, whereby the GABA content is retained. GABA may even be enriched depending on the treatment conditions. By this treatment, not only GABA but also active ingredients such as vitamins (in particular, water-soluble vitamins), minerals, and chlorophyll are retained. In addition, fading of the vivid green color of the green leaves and change in flavor are minimized.

In the thus-treated green grass leaves and processed products thereof, degeneration-related enzymes contained therein are inactivated, which enables the ingredients of the green leaves to be retained stably for a prolonged period of time. This also enables the vivid green color to be maintained. When such green leaves are used as a health food or a material for health food, the commercial value of the health food is increased.

Microwave treatment may be done with such conditions that degeneration-related enzymes are inactivated and/or the green color is not lost by heating. Such conditions can be appropriately determined by adjusting the microwave wavelength, the output power of a microwave irradiation apparatus, the irradiation time, and the like. In general, the frequency of such a microwave irradiation apparatus is 300 MHz to 30 GHz. The irradiation time is 0.5 to 10 minutes per 100 g (fresh weight, i.e., weight of fresh, undried leaves) of green grass leaves or processed products thereof (hereinafter, the term "green grass leaves" or "green leaves" may include processed products of the green grass leaves). For example, when a 2450 MHz, 500 W microwave is used, 100 g (fresh weight) of green grass leaves may be subjected to the microwave treatment for 0.5 to 10 minutes, preferably 0.5 to 5 minutes, and more preferably 0.5 to 1 minute. If the irradiation time is less than 0.5 minutes, the enzymes are only insufficiently inactivated, causing easy color fading of the treated green grass leaves. Also, ingredients naturally contained in the young leaves tend to be lost. If the irradiation time exceeds 10 minutes, GABA tends to decrease.

The GABA content increases when the microwave treatment time is within about one minute. As the treatment time lengthens, the GABA content decreases. Even if decreasing, however, 80% or more of the GABA content is still retained after a five-minute treatment.

In the method according to the present invention, a recommended procedure for retaining a high GABA content for a prolonged period of time is to use the anaerobic treatment and/or incubation treatment first, followed by the microwave treatment.

The thus-treated green leaves or processed products thereof are used for a desired purpose, for example, as a food material, a medicine material, or a feed, directly or after being further processed into an appropriate form. The treated green leaves or processed products thereof are in the form of green leaves, green leaf fragments, green leaf juice, green leaf extract, and the like. The green leaf fragments include cut products having a size easy to treat and green leaf slurry. The extract is obtained by adding a solvent usually used by those skilled in the art, such as water or an ethanol aqueous solution, to the treated green leaves or green leaf fragments and warming as required, to extract active ingredients. The extract includes extract liquid products and concentrated products thereof.

The treated green leaves, green leaf fragments, green leaf juice, and green leaf extract are dried as required. Drying is generally done so that the water content is reduced to 10% or less, preferably 5% or less. In the drying step, the treated green leaves, green leaf fragments, green leaf juice, and green leaf extract, for example, are dried by a method known to those skilled in the art, such as hot air drying, high-pressure steam drying, electromagnetic wave drying, spray drying, and freeze drying. Heat drying is done under such temperature and time conditions that the green leaves will not be discolored due to heating, i.e., preferably at 40 to 80° C., more preferably at 55 to 65° C. Slurry, extract, and juice of green grass leaves may be spray dried with the addition of an excipient such as dextrin, cyclodextrin, starch, or maltose as required.

The resultant dried products may be crushed by a method known to those skilled in the art using, for example, a crusher, mill, blender, stone mill, or the like. The crushed dried green leaves are sifted as required, to obtain, for example, those that have passed through a sieve having a 30 to 250 mesh. If the grain diameter of the crushed pieces is smaller than 250 mesh, further processing is difficult when they are used as a food material or a medicine material. If the grain diameter is larger than 30 mesh, uniform mixing with other food materials is difficult, for example.

The resultant products may be sterilized by a method known to those skilled in the art, such as air current sterilization, high pressure sterilization, and heating sterilization.

In the thus-treated green grass leaves or processed products thereof, the GABA content has been increased, or the high GABA content has been retained through the processing. The GABA content has usually been increased twofold or more, preferably threefold or more, and more preferably fivefold or more, compared with that of green leaves that were not treated by the method of the present invention.

For example, young leaves of a grass plant selected from barley, wheat, rye, oats, adlay, Italian ryegrass, and rice subjected to the GABA enriching treatment (anaerobic treatment and/or incubation treatment) contain GABA in an amount of at least 100 mg/100 g (based on fresh weight of leaves; 500 mg/100 g in terms of dry weight), usually 150 to 200 mg/100 g, preferably 300 mg/100 g or more, and more preferably 500 mg/100 g or more. The GABA content in just harvested young leaves is 80 mg/100 g at most. Therefore, the GABA content increases roughly twofold or more.

Young leaf powder of a grass plant selected from barley, wheat, rye, oats, adlay, Italian ryegrass, and rice produced through the microwave treatment, but not through the GABA enriching treatment, contains GABA in an amount of at least 20 mg/100 g (based on dry weight), usually 100 mg/100 g or more, preferably 200 mg/100 g or more, and more preferably 500 mg/100 g or more. Young leaf powder of the same plant produced through the GABA enriching treatment contains GABA in an amount of at least 50 mg/100 g (based on dry weight), usually 200 mg/100 g or more, preferably 500 mg/100 g or more, more preferably 1000 mg/100 g or more. For reference, the GABA content in young leaf powder of the same plant produced through the conventional hydrothermal treatment (i.e., blanching) is 10 mg/100 g (based on dry weight) at most.

Young leaf juice of a grass plant selected from barley, wheat, rye, oats, adlay, Italian ryegrass, and rice produced through the microwave treatment, but not through the GABA enriching treatment, contains the GABA in an amount of at least 10 mg/100 g (value in liquid weight; 400 mg/100 g in terms of dry weight), usually 20 mg/100 g or more, preferably 30 mg/100 g or more, and more preferably 50 mg/100 g or more.

Young leaf juice of the same plant produced through the GABA enriching treatment contains GABA in an amount of at least 20 mg/100 g (value in liquid weight; 800 mg/100 g in terms of dry weight), usually 30 mg/100 g or more, preferably 50 mg/100 g or more, and more preferably 100 mg/100 g or more. For reference, the GABA content in young leaf juice of the same plant produced through the conventional hydrothermal treatment is 2 mg/100 g (value in liquid weight) or less.

Young leaf juice powder of a grass plant selected from barley, wheat, rye, oats, adlay, Italian ryegrass, and rice, produced through the microwave treatment, but not through the GABA enriching treatment, contains GABA in an amount of at least 400 mg/100 g (based on dry weight), usually 800 mg/100 g or more, preferably 1200 mg/100 g or more, and more preferably 1600 mg/100 g or more. Young leaf juice powder of the same plant produced through the GABA enriching treatment contains GABA in an amount of at least 800 mg/100 g (based on dry weight), usually 1200 mg/100 g or more, preferably 2000 mg/100 g or more, and more preferably 4000 mg/100 g or more. For reference, the GABA content in young leaf juice powder of the same plant produced through the conventional hydrothermal treatment is 80 mg/100 g (dry weight) at most.

The green grass leaves or processed products thereof subjected to the above method to retain or increase the GABA content are also rich in active ingredients such as vitamins, minerals, and chlorophyll, compared with those obtained by conventional hot water blanching. For example, young leaf powder of a grass plant selected from barley, wheat, rye, oats, adlay, Italian ryegrass, and rice obtained according to the present invention contains: carotene usually twofold or more, preferably fivefold or more; vitamin $B_1$ usually fivefold or more, preferably tenfold or more; vitamin C usually 100-fold or more, preferably 200-fold or more; calcium usually twofold or more, preferably fivefold or more; potassium usually twofold or more, preferably fivefold or more; and chlorophyll usually twofold or more, preferably fivefold or more, compared with those obtained by the conventional method. In addition, since the vivid green color of the young leaves can be maintained through the treatment and also after the treatment, the value as a health food and a material for health food, for example, is high.

The green grass leaves or processed products thereof with the retained or increased GABA content can be used as materials for foods, drinks, medicines and a feed directly or by being mixed with an excipient, an extender, a binder, a thickener, an emulsifier, a colorant, a perfume, a food additive, a seasoning, and the like. For example, royal jelly, vitamins, proteins, calcium compounds, chitosan, lecithin, and the like may be mixed, and syrup and a seasoning may be added to correct the taste. The resultant products may be formed into capsules such as hard capsules and soft capsules, tablets, or pills, or otherwise in the shapes of powder, granules, tea leaves, tea bags, candy bars, or the like. These products may be ingested as they are, or dissolved in cold water, hot water, or milk for drinking. Otherwise, their ingredients may be leached out and ingested. The thus-obtained green grass leaves or processed products thereof may also be added to feed for animals such as livestock and pets.

Thus, according to the present invention, green grass leaves containing GABA at a high concentration are obtained. Thus, a pure GABA product can also be obtained from green grass leaves.

EXAMPLES

The following examples are merely illustrative and are by no means intended to limit the present invention.

Example 1

GABA enriching by incubation treatment
(1) Examination of incubation temperature Young barley leaves having a length of about 30 cm were picked, washed with water, and cut to about 10 cm pieces, to obtain about 100 g of young barley leaf pieces.

The resultant young barley leaves were placed in an incubator and left in a hot air atmosphere at a temperature shown in Table 1 below for one hour. The γ-aminobutyric acid (GABA) content in the resultant leaves was measured with an automatic amino acid analyzer under the following conditions:

[Operating conditions of automatic amino acid analyzer]
Machine type: JLC-500/V (JEOL Ltd.) Column: LCR-6, 4 mm×90 mm (JEOL Ltd.)
Mobile phase: lithium citrate buffer (JEOL Ltd.)
  P-21 (pH 2.98, Li 0.105 mol/l) 0–16.9 min.
  P-12 (pH 3.28, Li 0.26 mol/l) 16.3–36.1 min.
  P-13 (pH 3.46, Li 0.80 mol/l) 36.1–56.0 min.
  P-14 (pH 2.83, Li 1.54 mol/l) 56.0–63.4 min.
  P-15 (pH 3.65, Li 1.54 mol/l) 63.4–80.0 min.
Reactant: Ninhydrin hydridantin reagent (Wako Pure Chemical Industries, Ltd.)

| Temperature: | Column | 35° C. for 0 to 16.3 min. |
| | | 64° C. for 15.3 to 31.0 min |
| | | 44° C. for 31.0 to 44.4 min. |
| | | 72° C. for 63.4 to 80.0 min. |
| | Reaction vessel | 135° C. |
| Flow rate: | Mobile phase | 0.50 ml/min. |
| | Reaction mixture | 0.30 ml/min. |
| Measured wavelength: 570 nm | | |

The young barley leaves were dried due to the heat and air flow in the incubator, so that the apparent GABA content increases. Therefore, the water content of the treated young barley leaves was measured, and the GABA content of the treated young barley leaves was corrected by matching the post-treatment water content with the pre-treatment water content. The results are shown in Table 1. In Table 1, the GABA content represents the amount of GABA (mg) contained in 100 g of young barley leaves (fresh weight). The value inside the parentheses represents the amount of GABA (mg) in terms of dry weight. The GABA index represents the post-treatment GABA content (based on weight) with respect to the pre-treatment GABA content as 100.

TABLE 1

| Temperature (° C.) | GABA Content (mg) | GABA Index |
|---|---|---|
| Before Treatment | 60 (334) | 100 |
| 10 | 62 (345) | 103 |
| 20 | 144 (801) | 240 |
| 30 | 270 (1501) | 450 |
| 40 | 417 (2319) | 695 |
| 50 | 156 (867) | 260 |
| 60 | 66 (367) | 110 |

It can be seen from Table 1 that the GABA content in young barley leaves increases with the incubation treatment at a temperature of 20 to 50° C.

(2) Examination of incubation time

Young barley leaves were placed in an incubator and left in a hot air atmosphere kept at a temperature of 40° C. for a period shown in Table 2. The GABA content in the resultant leaves was measured, and the results are shown in Table 2 below. In Table 2, the GABA content represents the amount of GABA (mg) contained in 100 g of young barley leaves (fresh weight). The value inside the parentheses represents the amount of GABA (mg) in terms of dry weight. The GABA index represents the post-treatment GABA content (based on weight) with respect to the pre-treatment GABA content as 100.

TABLE 2

| Time | GABA Content (mg) | GABA Index |
|---|---|---|
| Before Treatment | 76 (423) | 100 |
| 10 minutes | 166 (923) | 218 |
| 30 minutes | 502 (2791) | 661 |
| 60 minutes | 511 (2841) | 672 |
| 6 hours | 498 (2769) | 655 |
| 12 hours | 504 (2802) | 663 |
| 24 hours | 479 (2663) | 630 |

It can be seen from Table 2 that the GABA content in young barley leaves increases with the incubation treatment for ten minutes and longer.

(3) Examination of incubation means

Young barley leaves were subjected to the incubation treatment by the use of hot air, by irradiation with infrared rays, or by the use of hot water at 40° C. for 60 minutes, and the GABA amount in the resultant leaves was measured.

In the irradiation with infrared rays, a 400 W infrared irradiator was disposed at such a distance from the young barley leaves that allowed the surface temperature of the leaves to be 40° C. In the treatment by the use of hot water, young barley leaves were immersed in hot water in a beaker and kept at 40° C.

The results are shown in Table 3 below. In Table 3, the GABA content represents the amount of GABA (mg) contained in 100 g of young barley leaves (fresh weight). The value inside the parentheses represents the amount of GABA (mg) in terms of dry weight. The GABA index represents the post-treatment GABA content (based on weight) with respect to the pre-treatment GABA content as 100.

TABLE 3

| Incubation Means | GABA Content (mg) | GABA Index |
|---|---|---|
| Before Treatment | 49 (272) | 100 |
| Hot Air | 338 (1879) | 690 |
| Infrared Rays | 323 (1796) | 659 |
| Hot Water | 289 (1607) | 590 |

It can be seen from Table 3 that the GABA content of young barley leaves increases for all the above incubation means.

Example 2

GABA enriching by anaerobic treatment

Young barley leaves as described in Example 1 were subjected to anaerobic treatment under the conditions shown in Table 4 below (temperature and time), and the GABA content in the resultant leaves was measured.

The anaerobic treatment was performed in the following manner. Young barley leaves were packed in a bag made of polyvinyl chloride, and the bag was deflated and then filled with nitrogen gas. The resultant bag including the leaves was kept in an incubator at the respective temperatures for the respective times shown in Table 4.

The results are shown in Table 4. In Table 4, the GABA content represents the amount of GABA (mg) contained in 100 g of young barley leaves (fresh weight). The value inside the parentheses represents the amount of GABA (mg) in terms of dry weight. The GABA index represents the post-treatment GABA content (based on weight) with respect to the pre-treatment GABA content as 100.

TABLE 4

| Temperature (° C.) | Time (hrs) | GABA Content (mg) | GABA Index |
|---|---|---|---|
| Before Treatment | | 52 | 100 |
| | | (289) | |
| 25 | 1 | 362 | 696 |
| | | (2013) | |
| | 12 | 387 | 744 |
| | | (2152) | |
| | 24 | 376 | 723 |
| | | (2091) | |
| 40 | 24 | 518 | 996 |
| | | (2880) | |

It can be seen from Table 4 that the GABA content in young barley leaves increases with the anaerobic treatment. In particular, the increase in GABA content is larger when the anaerobic treatment temperature is 40° C.

Example 3

Green leaves of wheat, rye, oats, adlay, Italian ryegrass and rice (cultivar Koshihikari) harvested at a length of about 20 cm were subjected to anaerobic treatment at 40° C. for six hours in the manner described in Example 2, and the GABA content of the resultant leaves was measured.

The results are shown in Table 5 below. In Table 5, the GABA content represents the amount of GABA (mg) contained in 100 g of the green leaves (fresh weight) before and after treatment. The value inside the parentheses represents the amount of GABA (mg) in terms of dry weight. The GABA index represents the post-treatment GABA content (based on weight) with respect to the pre-treatment GABA content as 100.

TABLE 5

| | GABA Content (mg) | | |
|---|---|---|---|
| | Before Treatment | After Treatment | GABA Index |
| Wheat | 48 | 153 | 319 |
| | (267) | (851) | |
| Rye | 39 | 210 | 538 |
| | (217) | (1168) | |
| Oats | 41 | 195 | 476 |
| | (228) | (1084) | |
| Adlay | 52 | 238 | 458 |
| | (289) | (1323) | |
| Italian Ryegrass | 24 | 118 | 492 |
| | (133) | (656) | |
| Rice (Koshihikari) | 39 | 211 | 541 |
| | (217) | (1173) | |

The above results indicate that the GABA content in green grass leaves is increased by the incubation treatment, the anerobic treatment, or the combination thereof.

Production examples: Production of young barley leaf powder and young barley leaf juice powder Young barley leaf powder and barley young leaf juice powder were produced in the following manner, and the GABA content of the powders was measured.

(1) Production of young barley leaf powder (standard product) including heat drying treatment Young leaves of barley harvested at a stem length of about 30 cm were used as the material. The leaves were washed with water to remove attached dirt and the like, and dried with hot air in a dryer (MOV-112S of Sanyo Electric Co., Ltd.) at 60° C. for six hours so as to have a reduced water content of 5% or less. The resultant leaves were crushed with a blender to such a degree that 90% of the crushed pieces passed through a 200 mesh sieve, to obtain young barley leaf powder as Product 1 (standard product). Product 1 contained GABA in an amount of 493 mg/100 g (dry weight).

(2) Production of young barley leaf powder including hydrothermal treatment (Comparative Production Example 1)

Young barley leaf powder was prepared according to the conventional production method (Japanese Patent No. 2544302) in the following manner. First, young barley leaves were washed with water to remove attached dirt and the like as in the above production example. The washed young barley leaves in an amount of 10 to 20 parts by volume were put in 100 parts by volume of a preheated aqueous solution containing 0.75 wt % of sodium chloride and 0.75 wt % of sodium hydrogencarbonate, and heated at 90 to 100° C. for three minutes (i.e., blanching was performed). The blanched young barley leaves were immediately immersed in 2 to 7° C. cold water for five minutes for cooling. The cooled young barley leaves were centrifuged for 30 seconds to remove some water. The dehydrated young barley leaves were then dried with hot air in a dryer at 60° C. for 6 hours so as to have a reduced water content of 5% or less. The dried leaves were crushed with a blender to such a degree that 90% of the crushed pieces passed through a 200 mesh sieve, to obtain young barley leaf powder as Product 2. Product 2 contained GABA in an amount of 8 mg/100 g (dry weight).

(3) Production of young barley leaf powder including microwave treatment (Production Examples 1 (1.1 to 1.5))

Five samples of young barley leaves washed as in Comparative Production Example 1 were subjected to microwave treatment using a 2450 MHz, 500 W power apparatus (microwave oven RE-121 of Sharp Corp.) for various times, i.e., 0.5, 1, 3, 5, and 10 minutes. The treated young barley leaves were dried in a dryer at 60° C. for 6 hours and then powdered with a blender, to obtain the young barley leaf powder as Products 3, 4, 5, 6, and 7 (Production Examples 1.1 to 1.5). The contents of GABA, vitamin $B_1$, and vitamin C in the resultant young barley leaf powder are shown in Table 6 below, together with these of Products 1 and 2. The respective contents of the ingredients are expressed in weights (mg) for 100 g of young barley leaves (in terms of dry weight). The content index of each ingredient represents the content (based on weight) of the ingredient with respect to the content of the said ingredient in Product 1 as 100.

TABLE 6

|  | Microwave Treatment (min.) | GABA Contents (mg/100 g) | Content Index | Vitamin $B_1$ Contents (mg/100 g) | Content Index | Vitamin C Contents (mg/100 g) | Content Index |
| --- | --- | --- | --- | --- | --- | --- | --- |
| Product 1 (Standard Product) | — | 493 | 100.0 | 1.09 | 100 | 690 | 100 |
| Product 2 (Comparative Production Example 1) | — | 8 | 1.6 | 0.09 | 8.3 | 8 | 1.2 |
| Product 3 (Production Example 1.1) | 0.5 | 583 | 118.3 | — | — | — | — |
| Product 4 (Production Example 1.2) | 1 | 586 | 118.9 | — | — | — | — |
| Product 5 (Production Example 1.3) | 3 | 413 | 83.8 | — | — | — | — |
| Product 6 (Production Example 1.4) | 5 | 412 | 83.6 | — | — | — | — |
| Product 7 (Production Example 1.5) | 10 | 41 | 8.3 | 1.00 | — | 476 | 69.0 |

The results show that the resultant young barley leaf powder contains GABA, vitamin $B_1$, and vitamin C in large amounts that are not observed in the young barley leaf powder produced by the conventional method. In addition, it was found that enzymes relating to color fading were inactivated so that the green color of the young barley leaf powder was kept unchanged. This was demonstrated by the following preservation stability test. The young barley leaf powder was sealed in an aluminum bag, and left to stand in an incubator kept in a warm atmosphere (40° C.) with a humidity of 70 to 75% for one month. An aluminum bag of the same powder product was separately stored in a cool place (10° C.). Vivid green color of each of the powders was maintained. The standard product obtained above was subjected to the same preservation stability test. In each of standard product powders preserved in an incubator (40° C.) and in a cool place (10° C.), the original green color was faded.

(4) Production of young barley leaf powder including GABA enriching treatment (Production Example 2)

Young barley leaves washed as in Comparative Production Example 1 were subjected to anaerobic treatment as a GABA enriching treatment in the manner described in Example 2. In this production example, the leaves were incubated at 40° C. for six hours. The resultant leaves were treated as described in Production Example 1 (microwave treatment). In the microwave treatment, the leaves were treated for one minute. The thus-treated young leaves were processed into leaf powder to obtain Product 8.

Table 7 shows the water content and the ingredient analysis results of Products 1, 2, 4, and 8 obtained as described above. Analyzing methods for the respective ingredients are as follows. (The units of the contents are wt % for water and mg/100 g for the other ingredients.)

Water: drying under reduced pressure and heating GABA: amino acid automatic analysis Total carotene: high-performance liquid chromatography Vitamin $B_1$: high-performance liquid chromatography Total vitamin C: high-performance liquid chromatography Calcium: potassium permanganate volumetric analysis Potassium: atomic absorption spectrophotometry Total chlorophyll: absorption spectrophotometry

TABLE 7

|  | Water (wt %) | GABA (mg/100 g) | Total Carotene (mg/100 g) | Vitamin $B_1$ (mg/100 g) | Vitamin C (mg/100 g) | Calcium (mg/100 g) | Potassium (mg/100 g) | Total Chlorophyll (mg/100 g) |
| --- | --- | --- | --- | --- | --- | --- | --- | --- |
| Product 1 | 2.1 | 482 | 75.4 | 1.09 | 690 | 790 | 4870 | 1245 |
| Product 2 | 2.3 | 8 | 13.6 | 0.09 | 3 | 336 | 1231 | 596 |
| Product 4 | 2.1 | 451 | 60.4 | 1.07 | 584 | 667 | 3952 | 1053 |
| Product 8 | 2.2 | 1421 | 61.9 | 1.01 | 573 | 678 | 3921 | 1021 |

It is apparent from Table 7 that the young barley leaf powder obtained according to the present invention include GABA, vitamins, minerals, and chlorophyll in larger amounts compared with those produced by the conventional method.

(5) Production of young barley leaf juice powder (Comparative Production Example 2)

Young barley leaves subjected to hot water treatment as in Comparative Production Example 1 were crushed with a mixer and filtered to obtain juice free from fiber contents. The juice was then freeze-dried to obtain young barley leaf juice powder. The GABA content of the resultant young barley leaf juice powder was 43 mg/100 g.

(6) Production of young barley leaf juice powder (Production Example 3)

Young barley leaves washed as in Comparative Production Example 1 were subjected to one-minute microwave treatment. The resultant leaves were crushed with a mixer and filtered to obtain juice free from fiber contents. The juice was then freeze-dried to obtain young barley leaf juice powder. The GABA content of the resultant young barley leaf juice powder was 612 mg/100 g.

(7) Production of young barley leaf juice powder including GABA enriching treatment (Production Example 4)

Young barley leaves washed as in Comparative Production Example 1 were subjected to anaerobic treatment as a GABA enriching treatment in the manner described in Example 2. In this production example, the leaves were incubated at 40° C. for six hours. The resultant leaves were treated in the manner described in Production Example 3 to obtain young barley leaf juice powder. The GABA content of the resultant powder was 3,012 mg/100 g.

Thus, as described above, the amount of GABA contained in green grass leaves can be increased by incubation treatment, anaerobic treatment, or a combination of these treatments. The resultant green leaves or processed products thereof, containing GABA at a high concentration, are excellent in preservation stability and palatability. Moreover, in addition to GABA, any of the active ingredients naturally contained in green grass leaves are retained in larger amounts compared with conventional products. Such green grass leaves or processed products thereof are excellent in their antihypertensive effect, whereby they can be used as materials for medicines, health food, animal feed and the like. Since the vivid green color of the green leaves is kept from fading, the commercial value as a health food or material therefor is high.

What is claimed is:

1. A method for retaining γ-aminobutyric acid in green grass leaves, comprising the step of subjecting green grass leaves or processed products thereof to microwave treatment.

2. A method according to claim 1, wherein the grass is at least one selected from the group consisting of barley, wheat, rye, oats, adlay, Italian ryegrass, and rice.

3. A method according to claim 2, wherein the grass is barley.

4. A method according to claim 1, wherein the green grass leaves containing retained or enriched γ-aminobutyric acid is in a form of green leaves, green leaf dried products, powder of green leaf dried products, green leaf fragments, dried green leaf fragments, green leaf juice, powder obtained from green leaf juice, green leaf extract, or powder obtained from green leaf extract.

5. A method according to claim 4, wherein the grass is barley.

6. A method for enriching and retaining γ-aminobutyric acid in green grass leaves, comprising the step of subjecting green grass leaves or processed products thereof to at least one treatment selected from the group consisting of incubation treatment and anaerobic treatment, followed by microwave treatment.

7. A method according to claim 6, wherein the grass is at least one selected from the group consisting of barley, wheat, rye, oats, adlay, Italian ryegrass, and rice.

8. A method according to claim 7, wherein the grass is barley.

9. A method according to claim 6, wherein the green grass leaves containing retained or enriched γ-aminobutyric acid is in a form of green leaves, green leaf dried products, powder of green leaf dried products, green leaf fragments, dried green leaf fragments, green leaf juice, powder obtained from green leaf juice, green leaf extract, or powder obtained from green leaf extract.

10. A method according to claim 9, wherein the grass is barley.

* * * * *